US006834994B2

(12) United States Patent
Ozawa et al.

(10) Patent No.: US 6,834,994 B2
(45) Date of Patent: Dec. 28, 2004

(54) X-RAY IMAGING APPARATUS FOR SUBTRACTION ANGIOGRAPHY

(75) Inventors: Masahiro Ozawa, Tochigi-ken (JP); Kunio Shiraishi, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/397,874

(22) Filed: Mar. 27, 2003

(65) Prior Publication Data

US 2003/0215055 A1 Nov. 20, 2003

(30) Foreign Application Priority Data

Apr. 3, 2002 (JP) ........................................ 2002-100757

(51) Int. Cl.⁷ ............................................... H05G 1/02
(52) U.S. Cl. .................................... 378/196; 378/197
(58) Field of Search ......................... 378/193, 195–198

(56) References Cited

U.S. PATENT DOCUMENTS 4,087,694 A * 5/1978 Hellstrom et al. .......... 378/195
5,020,089 A * 5/1991 Cramer et al. ............. 378/196
6,637,936 B2 * 10/2003 Crain et al. ................ 378/197

FOREIGN PATENT DOCUMENTS

| JP | 8-214216 | 8/1996 |
| JP | 9-66050 | 3/1997 |
| JP | 10-191 | 1/1998 |
| JP | 2002-291726 | 10/2002 |

* cited by examiner

*Primary Examiner*—Craig E. Church
*Assistant Examiner*—Jurie Yun
(74) *Attorney, Agent, or Firm*—Oblon, Spivak, McClelland, Maier & Neustadt, P.C.

(57) ABSTRACT

An X-ray imaging apparatus irradiates an X-ray every predetermined rotation angle of an arc arm for oppositely supporting an X-ray tube and an X-ray detector through a subject while the arc arm is reciprocated and rotated over a predetermined angle range. The X-ray imaging apparatus then acquires a mask image before injecting a contrast medium into the subject, and a contrast image after injecting the contrast medium. X-ray irradiation timing is controlled such that the collecting rate of an X-ray image in an acceleration/deceleration area near at least one of a start position and a stopping position of the arm is approximately equal to the collecting rate of the image in a constant velocity area for rotating the arm at an approximately constant velocity.

10 Claims, 11 Drawing Sheets

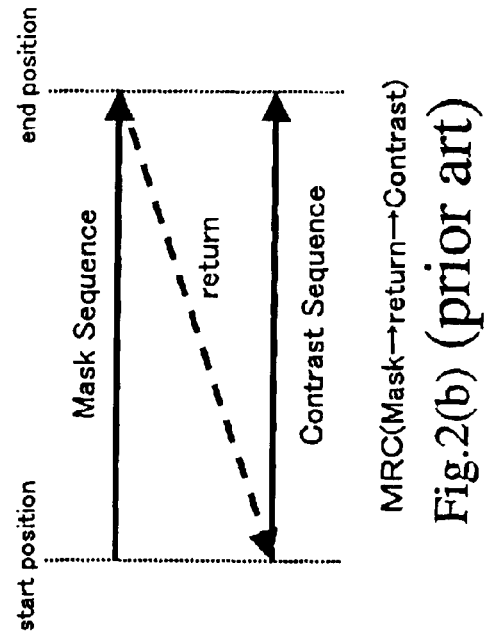
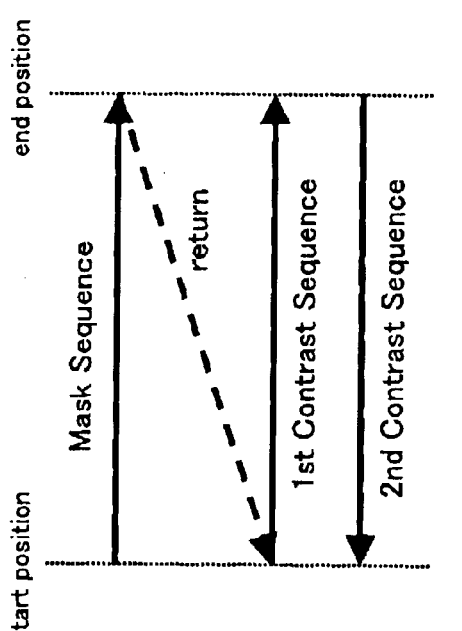
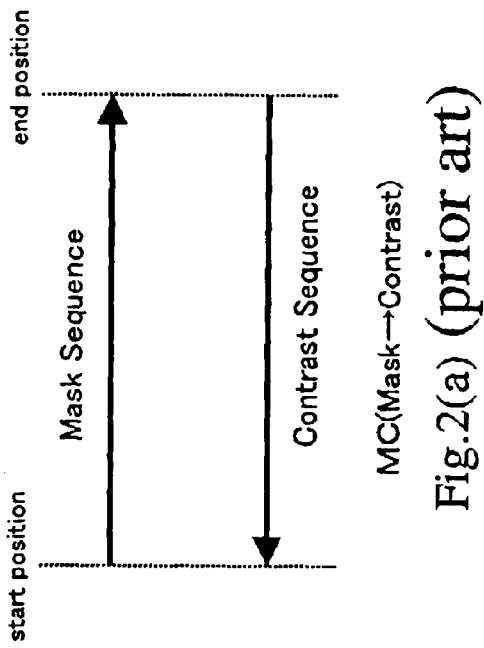
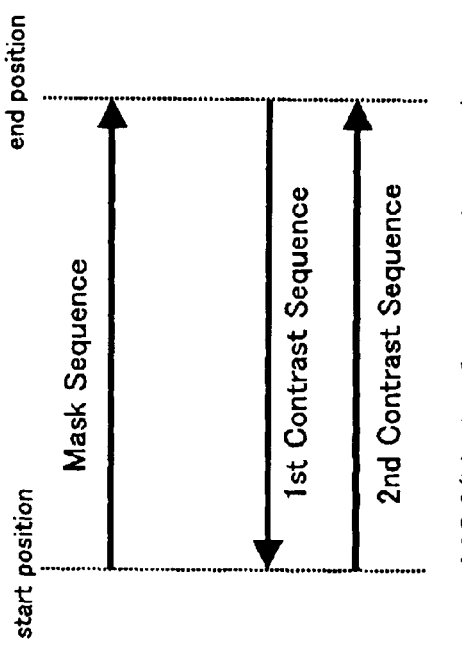
Fig.2(a) (prior art) MC(Mask→Contrast)
Fig.2(b) (prior art) MRC(Mask→return→Contrast)
Fig.2(c) (prior art) MCC(Mask→Contrast→Contrast)
Fig.2(d) (prior art) MRCC(Mask→return→Contrast→Contrast)

| Mask images | R01 | R2 | R03 | R1 | R2 | R3 |
|---|---|---|---|---|---|---|
| Contrast images | R4 | R5 | R6 | R7 | R8 | R9 |

Fig.9

| Mask Images | R1 | R2 | R3 | R4 | R2 | R6 |
|---|---|---|---|---|---|---|
| Contrast Images | R7 | R8 | R9 | R10 | R11 | R12 |

Fig.11

X-RAY IMAGING APPARATUS FOR SUBTRACTION ANGIOGRAPHY

CROSS-REFERENCE TO RELATED APPLICATIONS

This application is based upon and claims the benefit of priority from the prior Japanese Patent Application No. 2002-100757, filed on Apr. 3, 2002; the entire contents of which are incorporated herein by reference.

TECHNICAL FIELD

The present invention relates to an X-ray imaging apparatus for collecting a subtraction image by photographing a mask image and a contrast image while an arm for oppositely supporting an X-ray tube and an X-ray detector with a subject between is reciprocated and rotated over the range of a predetermined angle around the subject.

BACKGROUND OF THE INVENTION

A DSA (Digital Subtraction Angiography) image is collected when a blood vessel system, the blood vessels of internal organs, etc. are diagnosed. In a procedure for collecting this DSA image, the mask image is first photographed and is once stored to a memory before a contrast medium is injected. Next, the contrast medium is injected into the subject, and the contrast image is photographed and is also stored to the memory. Then, the mask image and the contrast image in the same position of the subject are read from the memory and both the images are subtraction-processed. Thus, the background such as bones, etc. is removed so that the DSA image left with respect to only a blood vessel image injecting the contrast medium thereinto is obtained.

The digital subtraction rotational angiography is known as a technique for obtaining a solid DSA image of the region of interest as well as the DSA image of a planar shape. In this technique, for example, the X-ray tube and the X-ray detector are oppositely supported at both ends of the arm formed in an arc shape or a C-shape, and an X-ray image is continuously photographed by rotating the arm around the subject rested between this X-ray tube and the X-ray detector. In such rotation photographing, the mask image before the injection of the contrast medium, and the contrast image after the injection of the contrast medium are photographed at the same angle, and a contrast blood vessel, etc. are displayed by subtraction-processing both the images. Thus, an image suitable for the diagnosis can be provided by easily grasping a solid shape.

The schematic construction of a conventional X-ray imaging apparatus for performing such digital subtraction rotational angiography is shown by a systematic view in FIG. 1.

As shown in FIG. 1, the conventional X-ray imaging apparatus has an X-ray tube 1 as an X-ray generator for irradiating an X-ray, an X-ray detector 2 for detecting this X-ray, an arm 3 for oppositely supporting the X-ray tube 1 and the X-ray detector 2 and formed in e.g., a C-shape, an arm driving unit 4 for holding the arm 3 and rotating this arm 3 with its holding axis as a center, and an angle detector 5 for detecting the rotation angle of the arm 3. Further, the conventional X-ray imaging apparatus has an A/D converter 6 for converting an image signal output from the X-ray detector 2 to a digital signal. The apparatus further includes an image memory 7 for recording the image signal converted to the digital signal through the A/D converter 6 and a subtraction module 8 for subtraction-processing plural image signals read from the image memory 7. The apparatus also has a D/A converter 9 for converting the image signal obtained by the subtraction processing in the subtraction module 8 to an analog signal, a display unit 10 for displaying an output of the D/A converter 9, a main controller 11, and an input device 12. The main controller 11 has an central processing unit (CPU) and a memory for controlling the irradiation of the X-ray from the X-ray tube 1, rotation control of the arm 3 using the arm driving unit 4, fetch of the image signal to the image memory 7 and reading of this image signal, subtraction processing of the image signal in the subtraction module 8, etc. The input device 12 has a keyboard, a mouse, a track ball, etc. for suitably inputting a set value, etc. to the main controller 11 by an operator. Further, the conventional X-ray imaging apparatus has a bed 13 for locating the subject placed on a tabletop between the X-ray tube 1 and the X-ray detector 2.

The X-ray detector 2 generally uses a type in which the X-ray image is converted to a visible light image by an image intensifier (hereinafter briefly called I.I.) and this visible light image is photographed by a television camera through an optical system for controlling the transmitting amount of the visible light image formed on the output fluorescent screen of the I.I. However, the X-ray detector 2 may be also constructed by a flat panel detector (hereinafter briefly called FPD) recently practically used and formed by a semiconductor array in which a switching element and a capacitor formed on e.g., a glass substrate are covered with a photoelectrically conductive film, etc. for converting the X-ray to an electric charge, etc. Since the output of this FPD is a digital signal, no A/D converter 6 is required when the FPD is used.

The procedure for executing the digital subtraction rotational angiography by such an X-ray imaging apparatus is as follows.

First, while the arm 3 is rotated over the angle range registered in advance around the subject lying on the bed 13 by giving the instructions of a photographing start from an operator through the input device 12, the X-ray is irradiated from the X-ray tube 1 and an X-ray photograph is taken. Thus, the image detected by the X-ray detector 2 is stored to the image memory 7. At this time, the above image is collected in the same angle range of the arm 3 before and after the contrast medium is injected. As a result, the mask image and the contrast image are obtained every angular position.

Next, in the subtraction module 8, the contrast image and the mask image collected at the same angle as this contrast image are subtraction-processed. This processing is continuously performed at each angle, and its result is displayed in the display unit 10 so that the regeneration of a rotation DSA image is realized.

An image collecting pattern is divided into four kinds of typical patterns as shown in FIG. 2 by the combination of rotating directions of the arm 3 at the collecting time of the mask image and the contrast image.

Namely, FIG. 2(A) shows a pattern in which the mask image is collected by a mask sequence from a rotation start position of the arm 3 to a rotation end position, and the arm 3 is subsequently returned from the rotation end position to the rotation start position and the contrast image is collected by a contrast sequence during this return. This pattern is called an MC mode.

FIG. 2(B) shows a pattern in which the mask image is collected by the mask sequence from the rotation start position of the arm 3 to the rotation end position, and a return operation for returning the arm 3 from the rotation end position to the rotation start position is then performed, and no X-ray is irradiated (no photographing operation is performed) during this return operation, and the arm 3 is subsequently again returned from the rotation start position, and the contrast image is collected by the contrast sequence while the arm 3 reaches the rotation end position from the rotation start position. This pattern is called an MRC mode.

In such MC and MRC modes, the X-ray is irradiated every predetermined angle in the predetermined rotation range of the arm 3, and the mask image and the contrast image are collected. The rotation DSA image is obtained by subtraction-processing both the mask and contrast images respectively photographed in the same angle position.

In contrast to this, similar to the MC mode, FIG. 2(C) shows a pattern in which the mask image is collected by the mask sequence from the rotation start position of the arm 3 to the rotation end position, and the contrast image is subsequently collected by the contrast sequence (a first contrast sequence) during the return of the arm 3 from the rotation end position to the rotation start position, and the contrast image is again collected by again returning the arm 3 from the rotation start position to the rotation end position by the contrast sequence (a second contrast sequence) during this return. This pattern is called an MCC mode.

Further, similar to the MRC mode, FIG. 2(D) shows the following pattern. Namely, in this pattern, the mask image is collected by the mask sequence from the rotation start position of the arm 3 to the rotation end position. Thereafter, a return operation for returning the arm 3 from the rotation end position to the rotation start position is performed. No X-ray is irradiated (no photographing or image acquisition operation is performed) during this return operation, and the arm 3 is subsequently again returned from the rotation start position. While the arm 3 reaches the rotation end position from the rotation start position, the contrast image is collected by the contrast sequence (a first contrast sequence), and the contrast image is again collected by again returning the arm 3 from the rotation end position to the rotation start position by the contrast sequence (a second contrast sequence) during this return. This pattern is called an MRCC mode.

Since the second contrast image is thus collected by the second contrast sequence in the MCC mode and the MRCC mode, the DSA image using the second contrast image can be also obtained. Accordingly, the MCC and MRCC modes have characters particularly effective to observe the degree of a blood flow in static venation of the injected contrast medium.

Next, the relation of a time change in the rotation angle of the arm 3 for collecting the mask image and the contrast image and the subtraction processing will be explained.

FIG. 3 is a typical view shown to explain an image collecting sequence in the MCC mode. Namely, when the arm 3 is set to be reciprocated and rotated between angles A and B, the interval between angles A and A' is an area for accelerating and decelerating the rotational speed of the arm 3. The interval between angles B' and B is also an area for decelerating and accelerating the rotational speed. These areas are called acceleration/deceleration areas. The interval between the angles A' and B' is a constant velocity area in which the rotational speed of the arm 3 is constant. Accordingly, when the rotation of the arm 3 is set to be started from the angle A, the arm 3 is accelerated in an area R1, and is rotated at a constant velocity in an area R2, and is further decelerated in an area R3. When the arm 3 reaches the angle B, the arm 3 is instantaneously stopped and the rotation direction of the arm 3 is then inverted and the arm 3 is accelerated from the angle B in an area R4. A reciprocating rotation operation is performed by repeating such operations.

When timing of the image collection in such a rotation angle range is seen in time, the mask image is collected in the acceleration/deceleration area R1 (acceleration), the constant velocity area R2 and the acceleration/deceleration area R3 (deceleration). The first contrast image is collected in the acceleration/deceleration area R4 (acceleration), a constant velocity area R5 and an acceleration/deceleration area R6 (deceleration). Further, the second contrast image is collected in an acceleration/deceleration area R7 (acceleration), a constant velocity area R8 and an acceleration/deceleration area R9 (deceleration). The mask image collected in the acceleration/deceleration area R1 (acceleration) is subtraction-processed with respect to each of the first contrast image collected in the acceleration/deceleration area R6 (deceleration) and the second contrast image collected in the acceleration/deceleration area R7 (acceleration). The mask image collected in the constant velocity area R2 is similarly subtraction-processed with respect to each of the first and second contrast images collected in the constant velocity areas R5, R8. Further, the mask image collected in the acceleration/deceleration area R3 (deceleration) is subtraction-processed with respect to each of the first contrast image collected in the acceleration/deceleration area R4 (acceleration) and the second contrast image collected in the acceleration/deceleration area R9 (deceleration). Thus, the rotation DSA image is obtained by these subtraction processings.

FIG. 4 is similarly a typical view shown to explain the image collecting sequence in the MRCC mode. The arm 3 is reciprocated and rotated between angles A and B. The interval between angles A and A' and the interval between angles B' and B are acceleration/deceleration areas. The interval between the angles A' and B' is a constant velocity area. In this case, similar to the MCC mode, the mask image is collected in the acceleration/deceleration area R1 (acceleration), the constant velocity area R2 and the acceleration/deceleration area R3 (deceleration). However, only a return operation of the arm 3 is performed and no photographing operation is performed in the acceleration/deceleration area R4, the constant velocity area R5 and the acceleration/deceleration area R6. The first contrast image is collected in the acceleration/deceleration area R7 (acceleration), the constant velocity area R8 and the acceleration/deceleration area R9 (deceleration). The second contrast image is subsequently collected in an acceleration/deceleration area R10 (acceleration), a constant velocity area R11 and an acceleration/deceleration area R12 (deceleration).

Further, the mask image collected in the acceleration/deceleration area R1 (acceleration) is subtraction-processed with respect to each of the first contrast image collected in the acceleration/deceleration area R7 (acceleration) and the second contrast image collected in the acceleration/deceleration area R12 (deceleration) to obtain the rotation DSA image later. The mask image collected in the constant velocity area R2 is similarly subtraction-processed with respect to each of the first and second contrast images collected in the constant velocity areas R8, R11. Further, the mask image collected in the acceleration/deceleration area R3 (deceleration) is subtraction-processed with respect to each of the first contrast image collected in the acceleration/ deceleration area R9 (deceleration) and the second contrast image collected in the acceleration/deceleration area R10 (acceleration).

The MC mode is a case in which no second contrast image is photographed (there is no photograph from R7 and R9) in the MCC mode. The MRC mode is a case in which no second contrast image is photographed (there is no photograph from R10 to R12) in the MRCC mode. Accordingly, since the subtraction processing relating to these patterns can be easily guessed from the above explanation, its explanation is omitted.

In the digital subtraction rotational angiography, an acceleration/deceleration area having no constant rotational speed of the arm 3 always exists just after the rotation start of the arm 3 and just before the rotation stoppage.

Further, when the mask image and the contrast image are subtraction-processed in the above respective patterns except for the MRC mode, there is a case in which the data of in conformity of the rotating direction of the arm 3 are subtraction-processed particularly in the acceleration/ deceleration area. Namely, this case corresponds to areas R1 and R6, areas R3 and R4 in the MCC mode and the MC mode, and areas R1 and R12, areas R3 and R10, etc. in the MRCC mode. In such an acceleration/deceleration area, no vibrating states of the arm 3 at the accelerating and decelerating times are conformed to each other in accordance with conditions of the state of the arm 3 and a spatial position, etc. at a returning point of the arm 3 at the reciprocating operation time. Therefore, even when the mask image and the contrast image collected at the same angle are subtraction-processed, an image shift, i.e., misregistration is generated. Therefore, there was a case in which an artifact was caused in the DSA image.

Further, in a system in which the X-ray is irradiated by generating a trigger every time the arm position during the rotation reaches a determined angle, the collecting rate of image data in the acceleration/deceleration area is reduced in comparison with the collecting rate in the constant velocity area in which the rotational speed is constant. Therefore, when the photographed image is regenerated, there is a disadvantage in that an observation is made such that an image regenerating speed in the acceleration/deceleration area is relatively increased. In contrast to this, when the photographed image is regenerated in conformity with the real time, there is a disadvantage in that the image is regenerated as an unnatural image having no frame since there are no image data. Thus, in the acceleration/ deceleration area, no situation of the actual blood vessel contrast could be correctly represented in the direction of a time axis.

With respect to such disadvantages, it is also considered that the image is collected only in the constant velocity area without setting the acceleration/deceleration area to an object of the image collection. However, when this method is applied to an image collecting sequence such as the MCC mode and the MRCC mode in which the contrast sequence is returned, the photographing is temporarily interrupted in the returning area. Therefore, discontinuity in time is caused so that this method is not suitable for the observation of a flow degree of the contrast medium.

BRIEF SUMMARY OF THE INVENTION

The X-ray imaging apparatus of the present invention is made in consideration of the above situation, and can reduce misregistration and help to prevent the generation of the artifact. Further, when the DSA image is regenerated in real time, this X-ray imaging apparatus can regenerate the DSA image as a more natural image having no feeling of physical disorder.

According to one aspect of the present invention, the present invention resides in an X-ray imaging apparatus comprising an X-ray generator for irradiating an X-ray to a subject; an X-ray detector for detecting the X-ray irradiated from the X-ray generator and transmitted through the subject; an arc arm for oppositely supporting the X-ray generator and the X-ray detector through the subject; an arm driving unit for rotating the arm around the subject; image acquiring components for collecting a mask image before the injection of a contrast medium into the subject and a contrast image after the injection of the contrast medium by the X-ray irradiated from the X-ray generator during the rotating operation of the arm, and obtaining a subtraction image from the mask image and the contrast image in the same position; and timing control components for controlling irradiation timings of the X-ray with respect to the rotation angle of the arm in a constant velocity area for approximately rotating the arm at a constant velocity, and an acceleration/deceleration area near a start position or a stopping position of the arm such that these irradiation timings in the constant velocity are and the acceleration/ deceleration area are different from each other.

Additional aspects of the invention will be set forth in the description which follows, and in part will be obvious from the description, or may be learned by practice of the invention. The aspects of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a view for explaining four kinds of typical and known image collecting patterns in the digital subtraction rotational angiography.

FIG. 9 is a table for explaining the correspondence of a mask image and a contrast image when subtraction processing is performed in the MCC mode according to an embodiment of the present invention.

FIG. 11 is a table for explaining the correspondence of the mask image and the contrast image when the subtraction processing is performed in the MRCC mode according to an embodiment of the present invention.

DETAILED DESCRIPTION OF THE INVENTION

The embodiment modes of an X-ray imaging apparatus in the present invention will next be explained in detail with reference to FIGS. 5 to 11.

Figure 1:
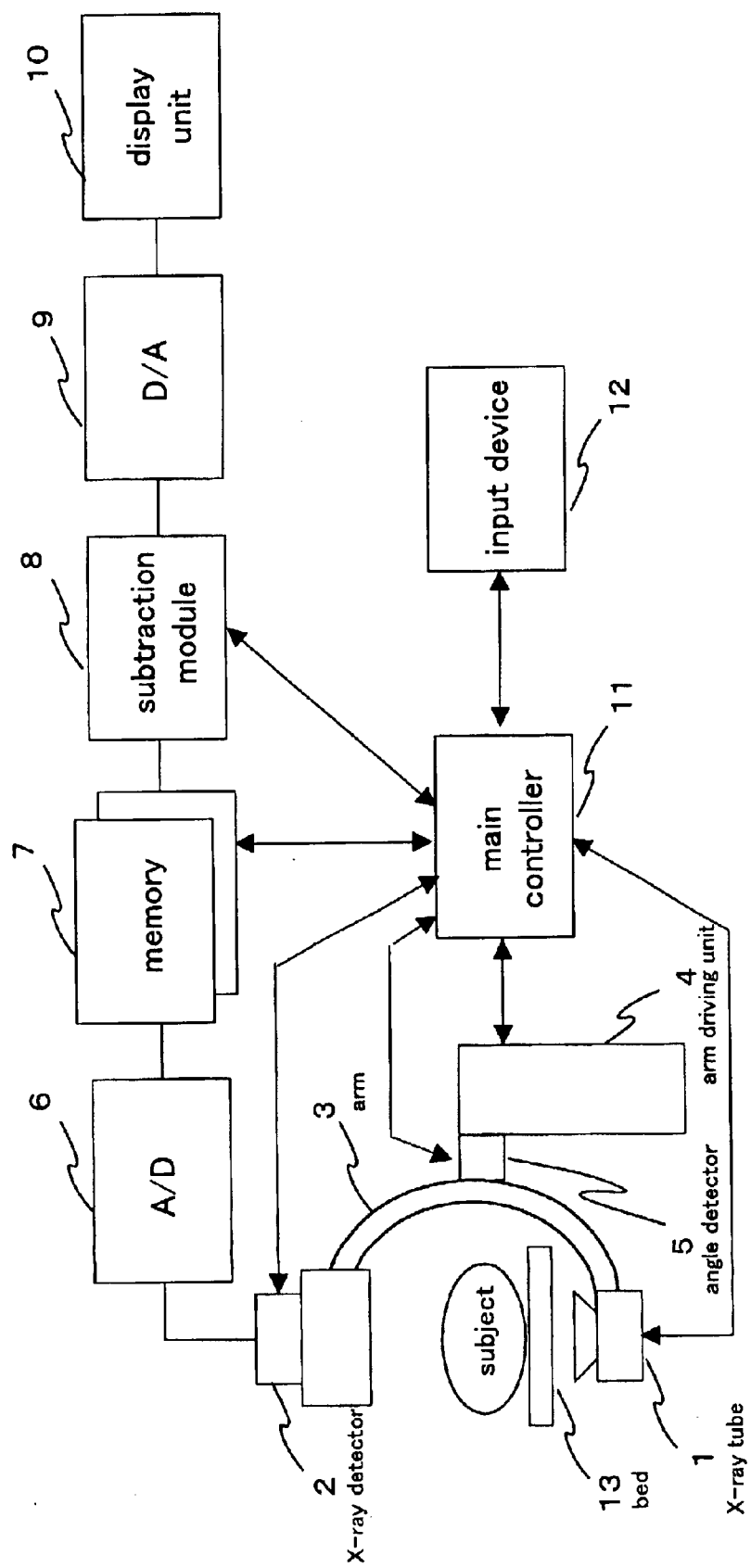
FIG. 1 is a view showing the schematic construction of a conventional X-ray imaging apparatus for performing the digital subtraction rotational angiography.
Figure 5:
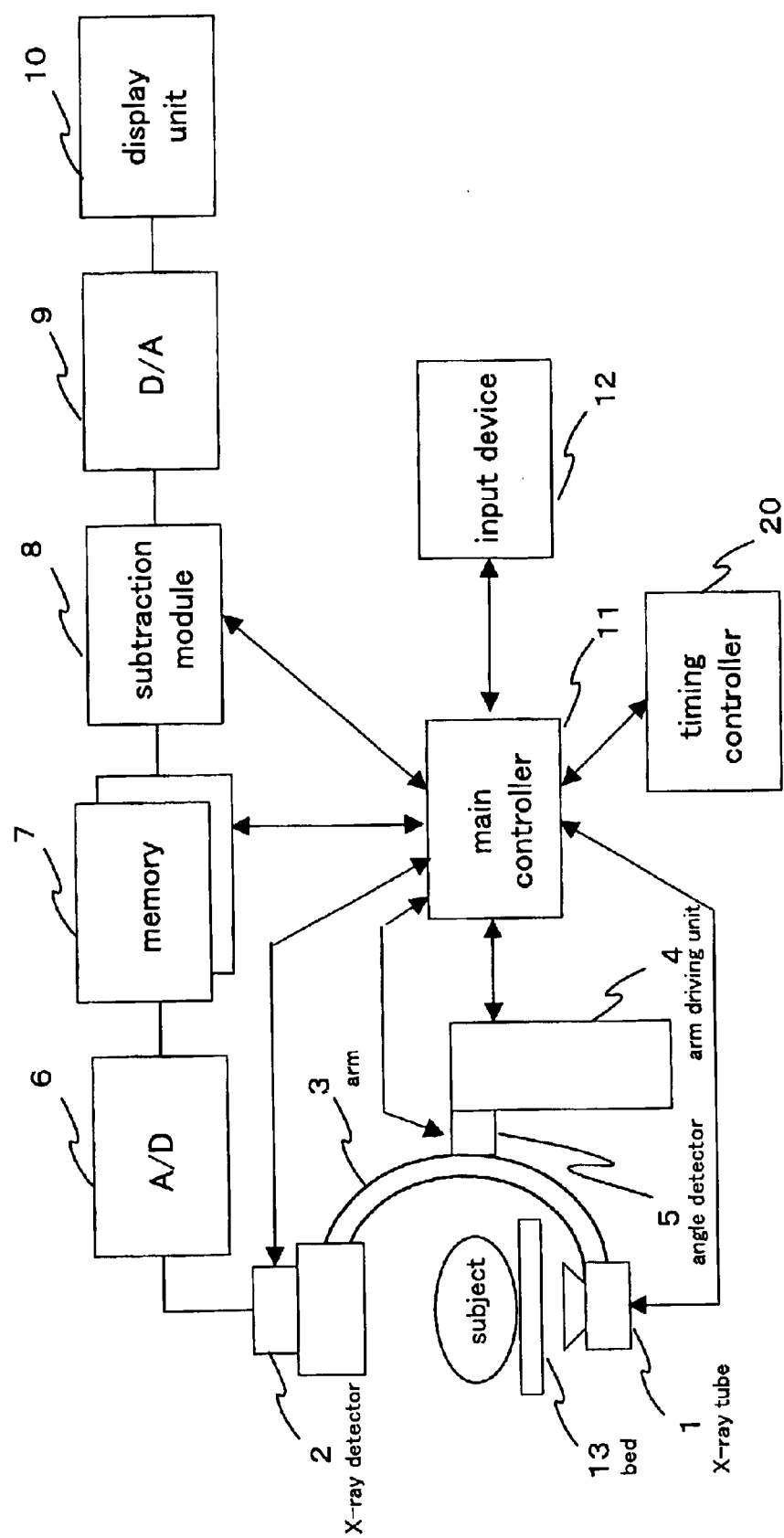
FIG. 5 is a view showing the schematic construction of an X-ray imaging apparatus according to an embodiment of the present invention.

FIG. 5 is a systematic view showing the schematic construction of the X-ray imaging apparatus according to an embodiment of the present invention. In the construction of the X-ray imaging apparatus according to this embodiment of the present invention, a timing controller 20 is added to the conventional X-ray imaging apparatus shown in FIG. 1. The other constructions are schematically similar to those in the conventional X-ray imaging apparatus. The operation of each portion is similar to that in the conventional X-ray imaging apparatus. Accordingly, in FIG. 5, the same portions as FIG. 1 are designated by the same reference numerals, and explanations of these portions are omitted. Aside from such similar portions, the apparatus includes an image memory 7, a subtraction module 8 and a main controller 11 that function as an image acquiring components.

The Timing controller 20 determines the irradiation timing of an X-ray on the basis of information obtained from an angle detector 5 for detecting the rotation angle of the arm 3. The main controller 11 is operated so as to operate an X-ray tube 1 in the timing determined in this Timing controller 20. The Timing controller 20 determines X-ray irradiation timings with respect to the rotating operation of the arm in an acceleration/deceleration area and a constant velocity area of the arm 3 such that these X-ray irradiation timings are different from each other. The angle detector 5, the main controller 11 and the Timing controller 20 function as a timing control components.

Figure 3:
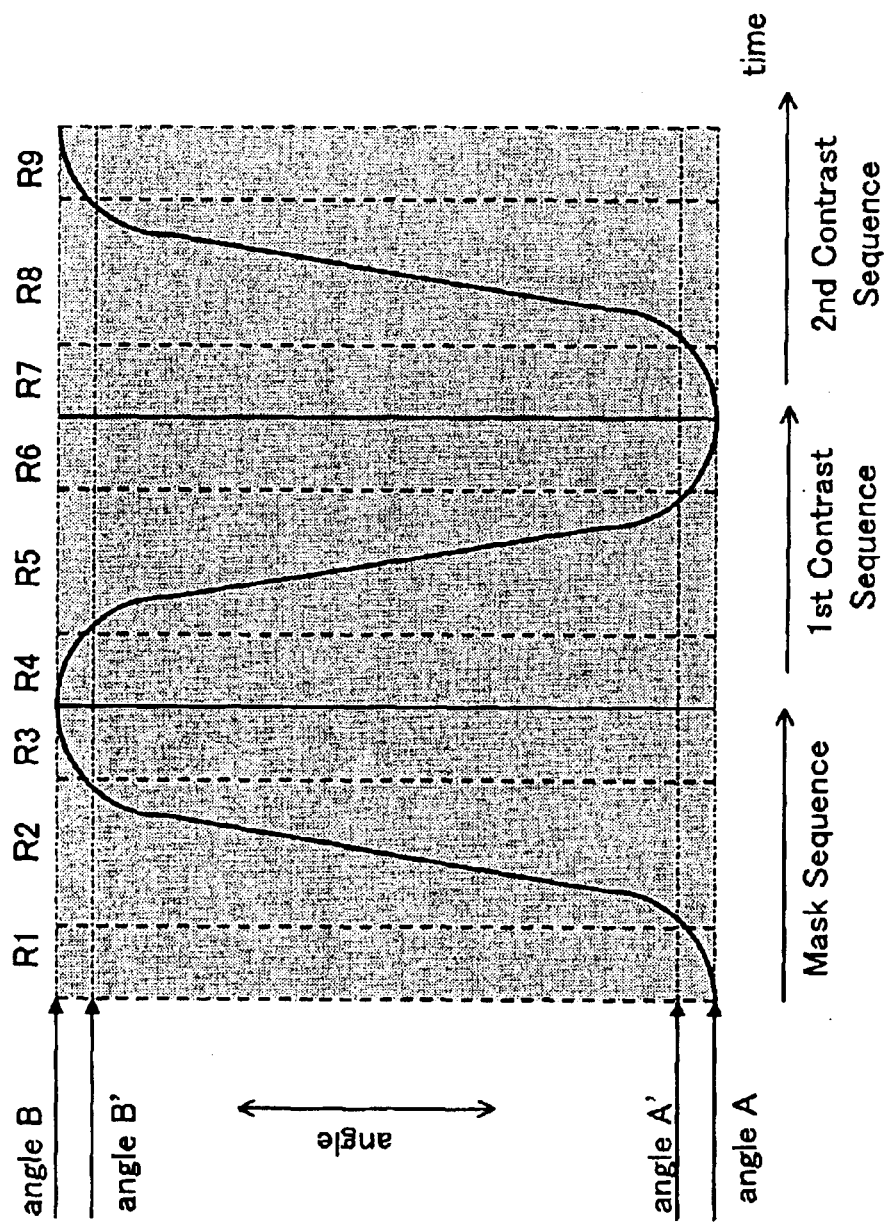
FIG. 3 is a view for explaining a conventional image collecting sequence in an MCC mode.
Figure 4:
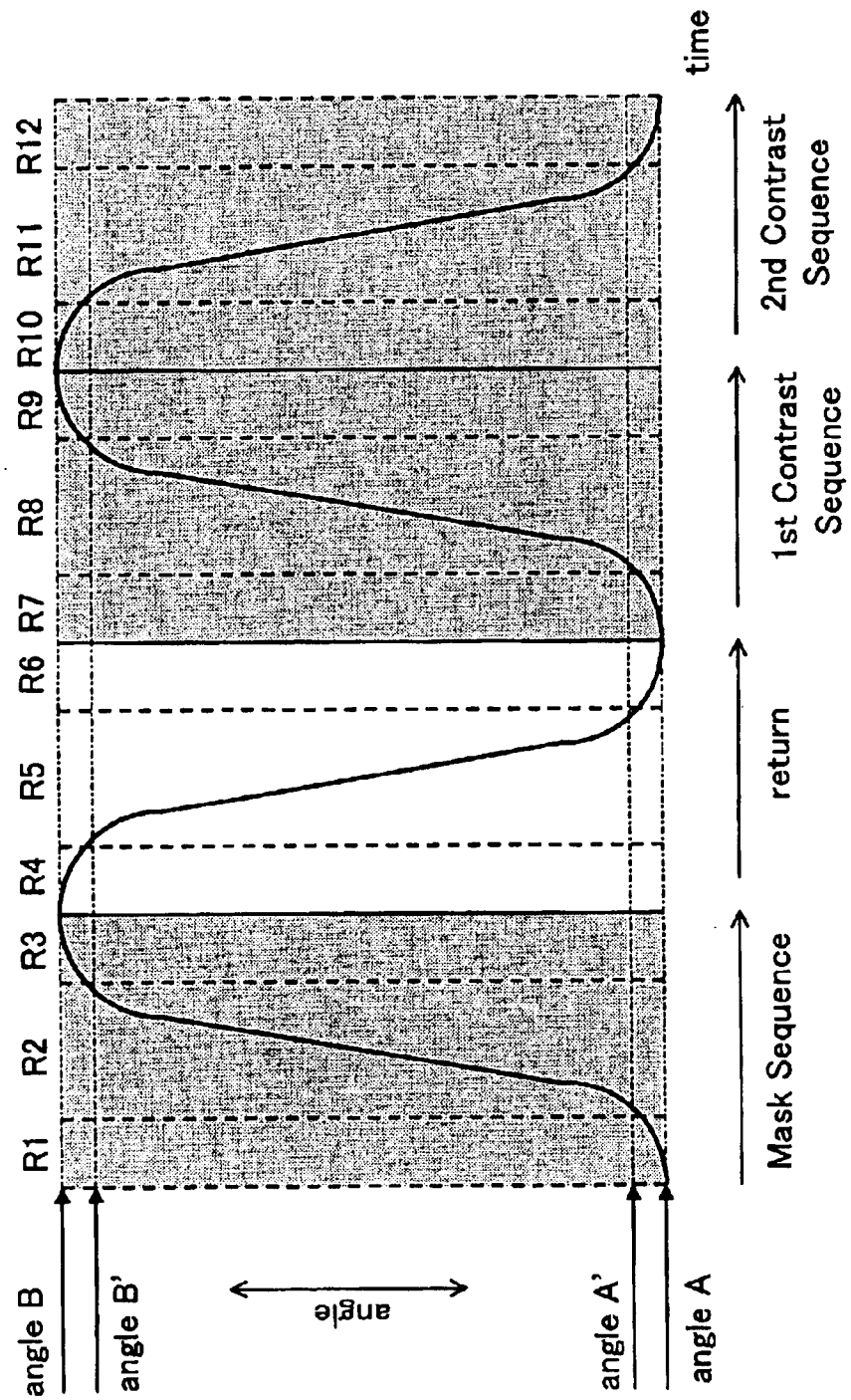
FIG. 4 is a view for explaining a conventional image collecting sequence in an MRCC mode.
Figure 6:
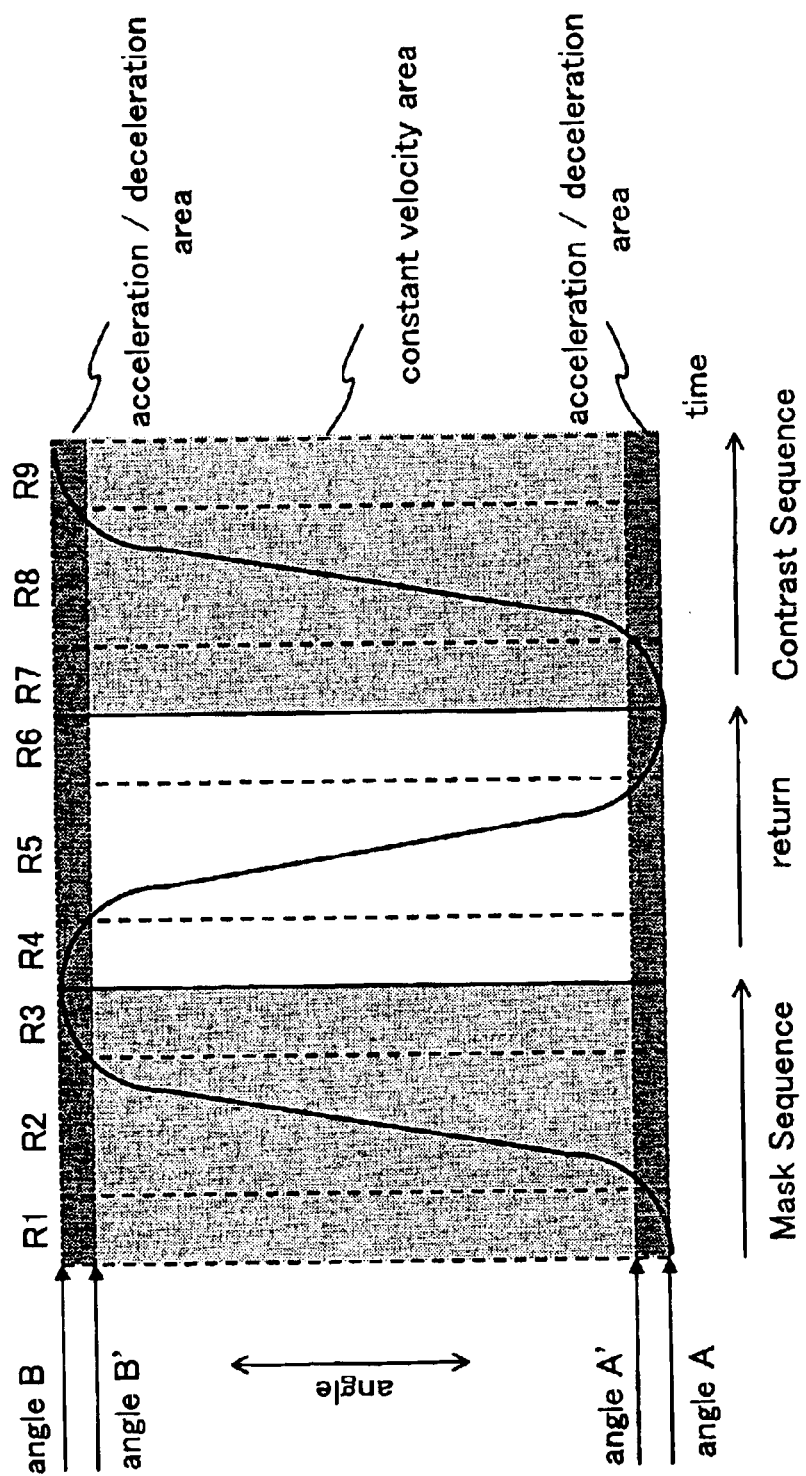
FIG. 6 is a view for explaining an image collecting sequence in an MRC mode according to an embodiment of the present invention.

FIG. 6 is a typical view showing an image collecting sequence in an MRC mode by a time change in the rotating angle of the arm 3. Similar to FIGS. 3 and 4, FIG. 6 shows an acceleration/deceleration area in which the arm 3 is reciprocated and rotated between angles A and B, and the rotational speed of the arm 3 is accelerated and decelerated between angles A and A' and between angles B' and B. The interval between the angles A' and B' is a constant velocity area in which the rotational speed of the arm 3 is constant. A mask image is collected in an acceleration/deceleration area R1 (acceleration), a constant velocity area R2 and an acceleration/deceleration area R3 (deceleration). Only a return operation of the arm 3 is performed and no photographing operation is performed in an acceleration/deceleration area R4, a constant velocity area R5 and an acceleration/deceleration area R6. A contrast image is then collected in an acceleration/deceleration area R7 (acceleration), a constant velocity area R8 and an acceleration/deceleration area R9 (deceleration). Such photographing timing is determined by the Timing controller 20, and is executed by supplying its signal to the main controller 11.

In an embodiment of the present invention, if the X-ray irradiation timing in the constant velocity area for rotating the arm 3 at a constant velocity is set to a certain angle, the X-ray irradiation timing in the acceleration/deceleration area can be finely set by stages to an angle smaller than that in the constant velocity area in accordance with the rotational speed of the arm 3 in the acceleration/deceleration area for accelerating or decelerating the arm 3. Such setting is performed in the Timing controller 20. This situation is shown by the typical view of FIG. 7. Namely, FIG. 7 shows the X-ray irradiation timings in the constant velocity area R8 and the acceleration/deceleration area R9 in FIG. 6 as one example.

Figure 7:
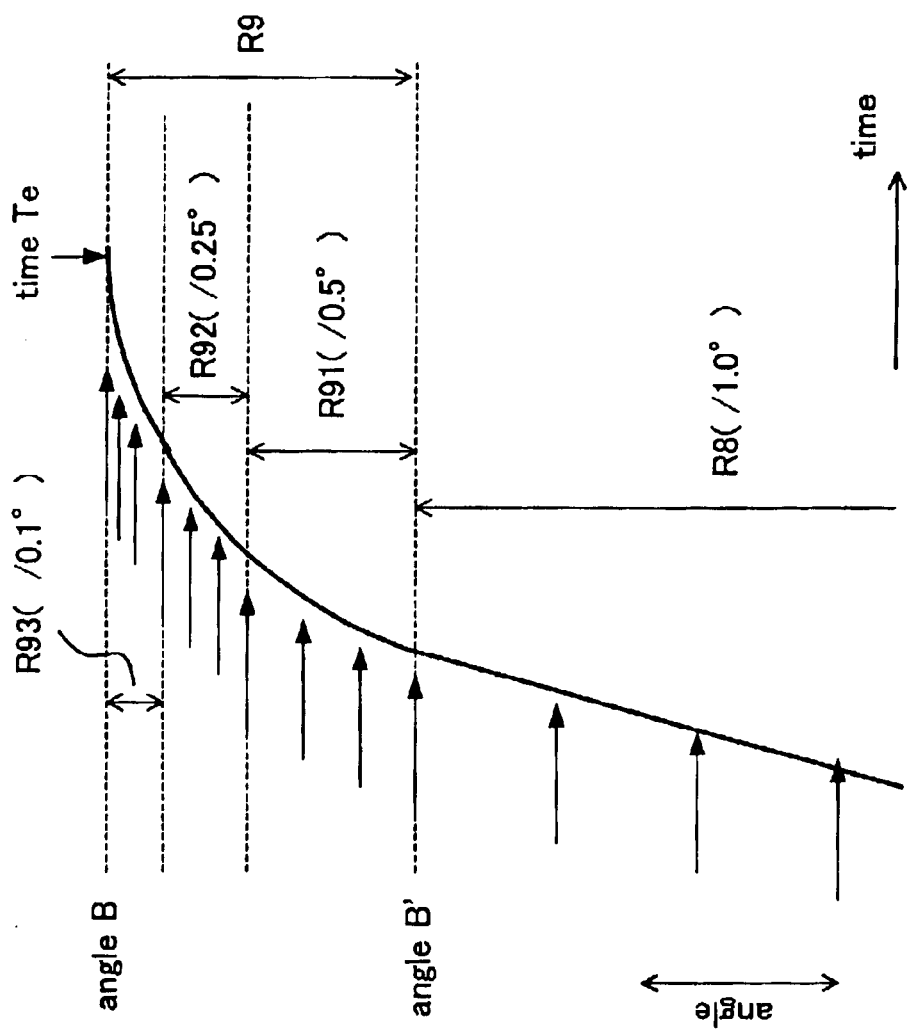
FIG. 7 is a view showing one example of X-ray irradiation timing in a constant velocity area and an acceleration/ deceleration area according to an embodiment of the present invention.

In the example shown in this FIG. 7, for example, a photograph is set to be taken in the constant velocity area R8 every rotation angle of 1.0 degree. For example, the acceleration/deceleration area R9 is divided into three areas of R91, R92 and R93. In the acceleration/deceleration area R91 of about ½ subsequent to the constant velocity area R8 among these three areas, the photograph is taken every rotation angle of 0.5 degree. In the subsequent further acceleration/deceleration area R92 of about ¼, the photograph is taken every rotation angle of 0.25 degree. Further, in the remaining acceleration/deceleration area R93, the photograph is taken every rotation angle of 0.1 degree.

The interval division in such acceleration/deceleration areas may be determined from operating characteristics of the arm 3, and may be also determined from the rotational speed of the arm 3 sequentially detected. In each case, the X-ray irradiation timing is determined such that the time series interval of the collected image is approximately equal to a collecting rate Tr of the image collected at the angle interval (e.g., every 1.0 degree) in the constant velocity area. Further, the above collecting rate Tr is set to the X-ray irradiation timing at an angle B in the acceleration/deceleration area R9 shown in FIG. 7 when the X-ray irradiation is also continued at the angle B (a stopping position of the arm 3) by the instructions of an operator after a time Te at which the arm 3 is stopped.

Further, in contrast to the constant velocity area for collecting the image at a constant angle interval, the image may be collected in the acceleration/deceleration area at a collecting rate equal to the time interval Tr at the collecting time of the image at the constant angle interval in the constant velocity area. In other words, the angle interval may differ in the acceleration/deceleration area to allow for collecting at a constant time interval Tr. In one example, when the rotational speed of the arm 3 is set to 30 degree/second and the angle interval of the image collection in the constant velocity area is set to 2.0 degree/frame, the image collecting rate in the constant velocity area corresponds to 15 frame/second. Accordingly, the image can be also collected at the collecting rate of 15 frame/second in the acceleration/deceleration area by irradiating the X-ray with 15 pulses for one second as a trigger in the acceleration/deceleration area. Thus, the image collection can be achieved at the rate equal to that in the constant velocity area.

These photographing timings in the constant velocity area and the acceleration/deceleration area in the X-ray imaging apparatus of embodiments of the present invention have been explained with respect to the constant velocity area R8 and the acceleration/deceleration area R9. However, the photographing timings are similarly set with respect to the other constant velocity area and acceleration/deceleration area. Further, the explanation of the MRC mode has been made, but the explanations of the other MC mode, MCC mode and MRCC mode are similar to the explanation of the MRC mode.

Thus, in accordance with the present invention, when a DSA image is regenerated in real time, the DSA image can be observed as a natural image by setting the collecting rate of the image with respect to time in the acceleration/deceleration area to be approximately equal to that in the constant velocity area.

An embodiment mode for reducing an image shift caused by a vibration of the arm in the acceleration/deceleration area of the arm will next be explained as another embodiment of the present invention.

Figure 8:
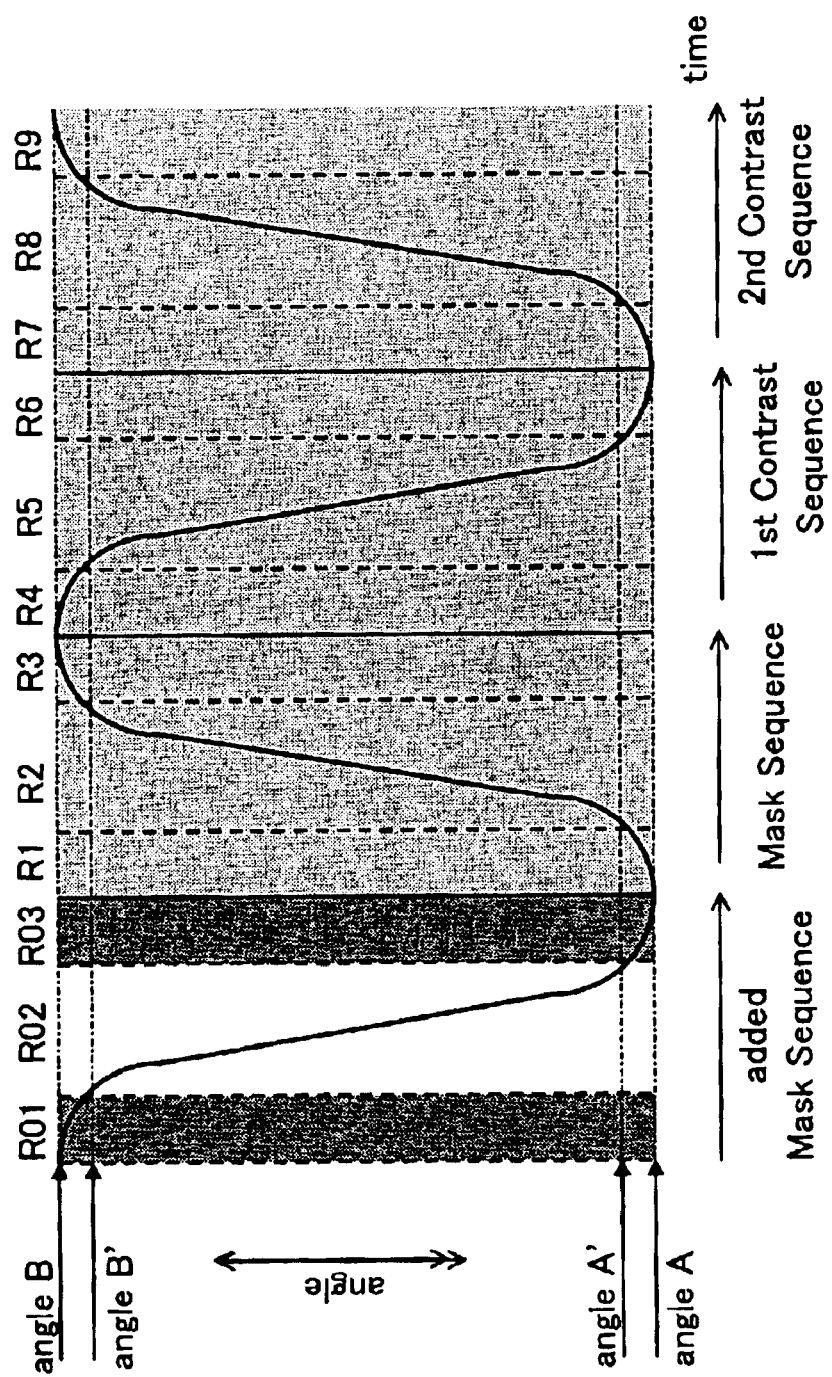
FIG. 8 is a view for explaining an image collecting sequence in the MCC mode according to an embodiment of the present invention.

FIG. 8 is a typical view shown to explain a case in which an embodiment of the present invention is applied to the image collection in the MCC mode. This embodiment mode is easily understood when FIG. 8 is referred in comparison with FIG. 3 shown as a conventional example.

Namely, in the MCC mode, as conventionally shown in FIG. 3, the mask image is collected in the acceleration/deceleration area R1 (acceleration), the constant velocity area R2 and the acceleration/deceleration area R3 (deceleration). The first contrast image is collected in the acceleration/deceleration area R4 (acceleration), the constant velocity area R5 and the acceleration/deceleration area R6 (deceleration). Further, the second contrast image is collected in the acceleration/deceleration area R7 (acceleration), the constant velocity area R8 and the acceleration/deceleration area R9 (deceleration). The acceleration, the constant velocity and the deceleration of the arm 3 are repeated between angles A and B and the arm 3 is reciprocated and rotated by the above collecting flow.

In contrast to this, in this embodiment, the arm 3 is started from before by one stroke prior to the collection of the mask image in the acceleration/deceleration area R1 (acceleration). Namely, if the conventional angle A is set to a rotation start position, an angle B is set to the rotation start position as shown in FIG. 8 in this embodiment. The mask image is added and collected in an acceleration/deceleration area R01 (acceleration) and an acceleration/deceleration area R03 (deceleration). Thereafter, similar to the conventional case, the mask image and the first and second contrast images are collected during the interval from R1 to R9. No image is collected in a constant velocity area R02.

Subtraction processing of the mask image and the first and second contrast images collected in this way is correspondingly performed with respect to each acceleration/deceleration area. This includes the accelerating area near the angle A, the decelerating area near the angle A, the accelerating area near the angle B, the decelerating area near the angle B, and the constant velocity area as shown by the table of FIG. 9. Namely, the correspondence is performed such that the mask image of the area R01 is subtraction-processed with respect to the contrast image of the area R4, and the mask image of the area R2 is subtraction-processed with respect to the contrast image of the area R5, and the mask image of the area R03 is subtraction-processed with respect to the contrast image of the area R6 (hereinafter omitted).

It is understood from these FIGS. 9 and 8 that the rotating direction of the arm 3 is the same in the accelerating areas R01 and R4 near the angle A, the decelerating areas R03 and R6 near the angle A, the accelerating areas R1 and R7 near the angle B, and the decelerating areas R3 and R9 near the angle B respectively corresponding to each other for the subtraction processing. Thus, in an embodiment of the present invention, with respect to the mask image and the contrast image, data showing conformity of the rotating direction of the arm 3 are always subtracted from each other in the subtraction processing, particularly in the acceleration/deceleration area. Accordingly, even when no vibrating states of the arm at the accelerating and decelerating times are conformed to each other, its influence is not exerted so that an image shift, i.e., misregistration is not caused by the subtraction processing. Therefore, the generation of an artifact in the DSA image can be prevented.

There is almost no fear that the vibrating state is changed in the constant velocity area even when the rotating direction of the arm 3 is different. Accordingly, no mask image is collected in the added constant velocity area R02 and the mask image obtained in the constant velocity area R2 is utilized in the subtraction processing with respect to the first and second contrast images so as to reduce the X-ray exposure of a subject.

Figure 10:
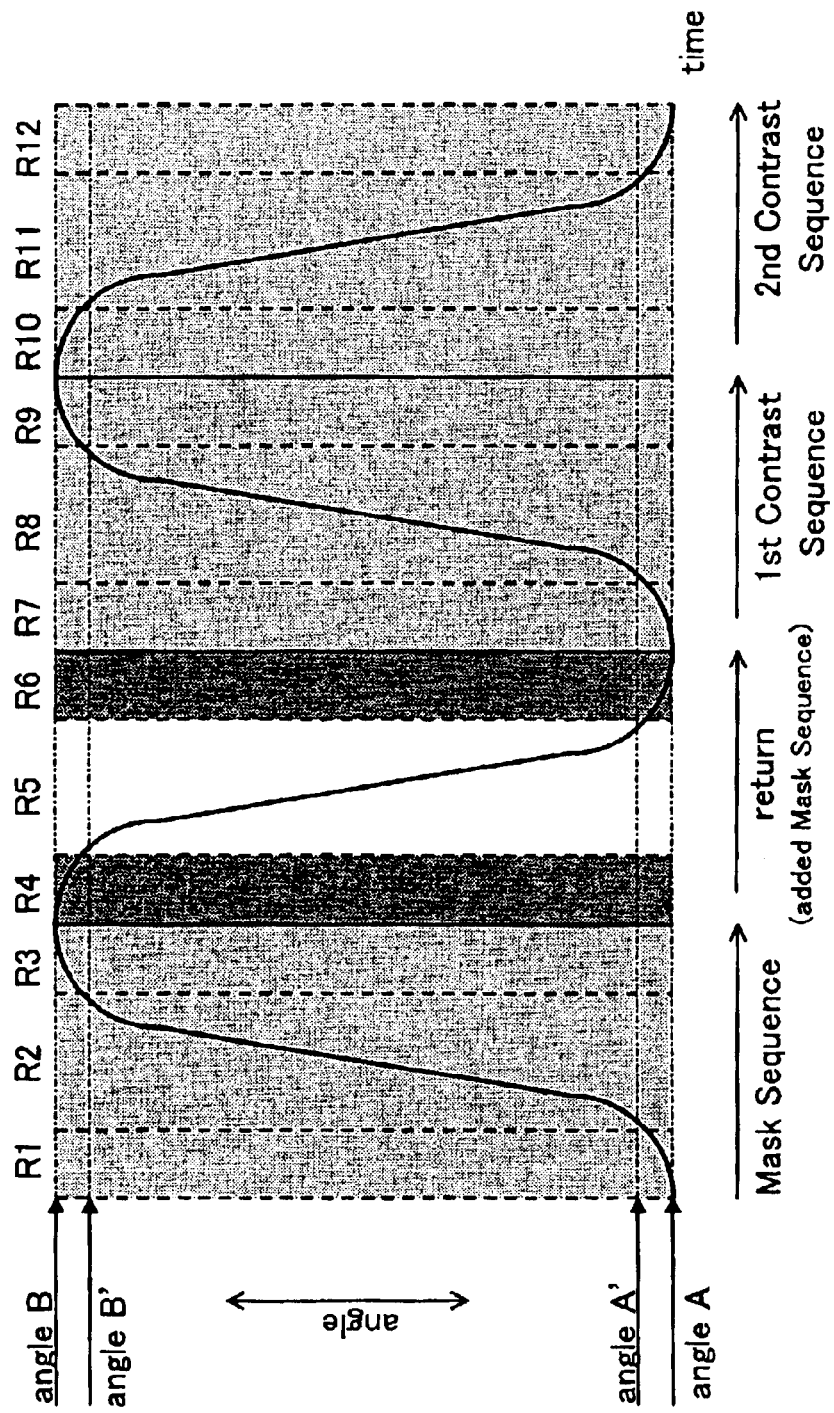
FIG. 10 is a view for explaining an image collecting sequence in the MRCC mode according to an embodiment of the present invention.

In the case of the MRCC mode, in an embodiment of the present invention, as shown by the typical view of FIG. 10, the mask image is also collected in the acceleration/deceleration area R4 (acceleration) and the acceleration/deceleration area R6 (deceleration) during the return operation.

Namely, in the conventional MRCC mode, as shown in FIG. 4, similar to the MCC mode, the mask image is collected in the acceleration/deceleration area R1 (acceleration), the constant velocity area R2 and the acceleration/deceleration area R3 (deceleration). Only the return operation of the arm 3 is performed and no photographing operation is performed in the subsequent acceleration/deceleration area R4, constant velocity area R5 and acceleration/deceleration area R6. However, in the present invention, as shown in FIG. 10, the mask image is also collected in the acceleration/deceleration area R4 (acceleration) and the acceleration/deceleration area R6 (deceleration) during the return operation. However, no mask image is collected in the constant velocity area R5 for reasons similar to those of the constant velocity area R02 in the case of the MCC mode shown in FIG. 8.

As shown by the table of FIG. 11, the subtraction processing of the mask image and the first and second contrast images collected in this way is correspondingly performed in each acceleration/deceleration area every the accelerating area near the angle A and the decelerating area near the angle A, the accelerating area near the angle B and the decelerating area near the angle B, and the constant velocity area. Namely, the correspondence is performed such that the mask image of the area R1 is subtraction-processed with respect to the contrast image of the area R7, and the mask image of the area R2 is subtraction-processed with respect to the contrast image of the area R8, and the mask image of the area R3 is subtraction-processed with respect to the contrast image of the area R9 (hereinafter omitted).

Accordingly, in the case of the MRCC mode, in the present invention, it is also understood from FIGS. 11 and 10 that the rotating direction of the arm 3 is the same in the accelerating areas R1 and R7 near the angle A, the decelerating areas R3 and R9 near the angle A, the accelerating areas R4 and R10 near the angle B, and the decelerating areas R6 and R12 near the angle B respectively corresponding to each other for the subtraction processing. The mask image and the contrast image in this area of the same rotating direction of the arm 3 are subtraction-processed. Accordingly, in this case, even when no vibrating states of the arm are conformed to each other at the accelerating and decelerating times, its influence is not exerted so that an image shift due to the subtraction processing, i.e., misregistration is not caused. Therefore, the generation of an artifact in the DSA image can be prevented.

Other embodiments of the present invention will be apparent to those skilled in the art from consideration of the specification and practice of the invention disclosed herein. It is intended that the specification and example embodiments be considered as exemplary only, with a true scope and spirit of the invention being indicated by the following claims.

What is claimed is:

1. An X-ray imaging apparatus comprising:
   an X-ray generator configured to irradiate an X-ray to a subject;
   an X-ray detector configured to detent the X-ray irradiated from said X-ray generator and transmitted through said subject;
   an arc arm configured to oppositely support said X-ray generator and said X-ray detector;
   an arm driving unit configured to rotate said arm in a rotation area around said subject, the rotation area including a constant velocity area where said arm is rotated at an approximate constant velocity and an acceleration/deceleration area near at least one of a start position and a stopping position of rotation of said arm;
   a timing control unit configured to control the X-ray generator to irradiate the X-ray at a first interval in the constant velocity area and irradiate the X-ray at a second interval that is different from the first interval in the acceleration/deceleration area; and
   an image memory unit configured to store a first mask image corresponding to the X-ray irradiated at the first interval and a second mask image corresponding to the X-ray irradiated at the second interval before injecting a contrast medium into said subject, and store a first contrast image corresponding to the X-ray irradiated at the first interval and a second contrast image corresponding to the X-ray irradiated at the second interval after injecting said contrast medium, and
   a subtraction unit configured to perform subtraction processing on the first mask image and the first contrast image and perform subtraction processing on the second mask image and the second contrast image.

2. The apparatus according to claim 1, wherein:
   said timing control unit is configured to control irradiation timings of the X-ray such that the second interval is narrower than the first interval.

3. The apparatus according to claim 2, wherein:
   said timing control unit is configured to control irradiation timings of the X-ray in said acceleration/deceleration area such that the second interval is set to a different angle interval in accordance with a rotational speed of said arm in said acceleration/deceleration area.

4. The apparatus according to claim 3, wherein:
   said timing control unit is configured to control the irradiation timings in said acceleration/deceleration area such that said acceleration/deceleration area is divided into a plurality of sub-areas determined in accordance with the rotational speed of said arm.

5. The apparatus according to claim 1, wherein:
   said timing control unit is configured to control irradiation timings of the X-ray such that the first interval is determined based on an angle of irradiation of the X-ray and the second interval is determined based on a time interval corresponding to the irradiation of the X-ray at the first interval.

6. The apparatus according to claim 1, wherein: said timing control unit is configured to control irradiation timings of the X-ray at the time of a stopping state of said arm in said acceleration/deceleration area so as to be set every time interval based on the irradiation timings of the X-ray in said constant velocity area.

7. The apparatus according to claim 1, wherein
   said image acquiring unit is configured to separately acquire said mask image and said contrast image while said arm is respectively reciprocated once via an acceleration for starting the arm, a constant velocity area in which the arm is rotated at an approximately constant velocity, and a deceleration area for stopping the arm, and
   said image acquiring unit is configured to perform subtraction processing to obtain the subtraction image using said mask image and said contrast image acquired in the same rotation direction and the same rotation angle of said arm.

8. The apparatus according to claim 7, wherein
   said image acquiring unit is configured to use said mask image acquired in one of a first constant velocity area and a second constant velocity area formed during one reciprocation of said arm in the subtraction processing, and wherein said image acquiring unit is configured to use said contrast image acquired in said constant velocity area.

9. The apparatus according to claim 8, wherein
   said X-ray generator is configured to stop the irradiation of the X-ray so as not to acquire said mask image in one of the first constant velocity area and the second constant velocity area formed during one reciprocation of said arm.

10. A method for obtaining an X-ray image, comprising:
    collecting a first mask image corresponding to X-ray irradiated at a first interval in a constant velocity area where an arm supporting an X-ray generator and an X-ray detector is rotated at an approximate constant velocity, before injecting a contrast medium into said subject;
    collecting a second mask image corresponding to X-ray irradiated at a second interval, that is different from the first interval, in an acceleration/deceleration area near at least one of a start position and a stopping position of rotation of said arm, before injecting a contrast medium into said subject;
    collecting a first contrast image corresponding to X-ray irradiated at the first interval in the constant velocity area, after injecting the contrast medium into said subject;
    collecting a second contrast image corresponding to X-ray irradiated at the second interval in the acceleration/deceleration area, after injecting a contrast medium into said subject;
    subtracting the first mask image and the first contrast image; and
    subtracting the second mask image and the second contrast image.

* * * * *